United States Patent [19]

Preuss et al.

[11] 4,284,621

[45] Aug. 18, 1981

[54] AGENTS FOR PROTECTION AGAINST LIGHT

[75] Inventors: Reinhard Preuss, Krefeld; Egbert Charlet, Roesrath; Peter Finkel, Cologne; Hans J. Rosenkranz, Krefeld, all of Fed. Rep. of Germany

[73] Assignee: Bayer Aktiengesellschaft, Leverkusen, Fed. Rep. of Germany

[21] Appl. No.: 24,742

[22] Filed: Mar. 28, 1979

[30] Foreign Application Priority Data

Apr. 18, 1978 [DE] Fed. Rep. of Germany ....... 2816819

[51] Int. Cl.³ .......................... A61K 7/42; A61K 7/44
[52] U.S. Cl. ........................ 424/59; 424/47; 424/60; 424/61; 424/63; 424/168
[58] Field of Search ................................. 424/59, 60

[56] References Cited

U.S. PATENT DOCUMENTS

| | | | |
|---|---|---|---|
| 2,334,348 | 11/1943 | Miglarese | 424/59 |
| 3,095,422 | 6/1963 | Duennenberger et al. | 424/59 X |
| 3,215,724 | 11/1965 | Strobel et al. | 424/59 X |
| 3,256,312 | 6/1966 | Strobel et al. | 424/59 X |
| 3,272,810 | 9/1966 | Strobel et al. | 424/59 X |
| 3,272,855 | 9/1966 | Strobel et al. | 424/59 X |
| 3,275,520 | 9/1966 | Strobel et al. | 424/59 |
| 3,381,006 | 4/1968 | Suh et al. | 424/59 X |

FOREIGN PATENT DOCUMENTS

| | | | |
|---|---|---|---|
| 1087902 | 8/1960 | Fed. Rep. of Germany | 424/59 |
| 66259 | 7/1967 | Fed. Rep. of Germany | 424/59 |
| 2358740 | 6/1975 | Fed. Rep. of Germany | 424/59 |

*Primary Examiner*—Dale R. Ore
*Attorney, Agent, or Firm*—Sprung, Felfe, Horn, Lynch & Kramer

[57] ABSTRACT

The invention concerns agents for protecting the skin against UV-radiation, said agents comprising an oil or wax having dissolved therein a compound of the formula

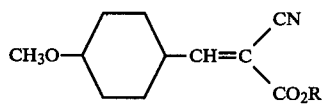

in which R is an n-hexyl, n-octyl or n-decyl radical or a primary isoalkyl radical with 9 or 10 carbon atoms.

8 Claims, No Drawings

AGENTS FOR PROTECTION AGAINST LIGHT

The present invention relates to agents for protecting the skin against UV radiation.

Solar radiation comprises, inter alia, the region of ultraviolet radiation, which can be divided into various areas with regard to action on human skin:

(a) on people with normal skin, UV radiation of wavelengths in the range from 285 to 320 nm (nanometers) (UV-B region) causes sunburn (erythema) and, due to photo-induced melanogenesis, subsequent pigmentation (indirect pigmentation).

(b) UV radiation of wavelengths in the range from 320 to 400 nm (UV-A region) causes rapid, poorly developed brown coloration (direct pigmentation). This pigmentation is due to photo-oxidation of certain precursors of melanin present in the skin.

The customary agents for protection against sunlight contain substances which absorb UV-B radiation to a greater or lesser extent. However, for people who are particularly sensitive to light and in order to restrict the overall exposure of the skin to UV radiation to a healthy level in the case of relatively intense solar radiation, agents for protection against sunlight which also contain substances which absorb UV-A radiation (UV-A filters) are necessary.

In addition to their use in cosmetic agents for protection against sunlight, UV-A filters are also of interest in dermatology, for those formulations which can be used for the chemotherapy of chronic damage caused by light, of psoriasis and of industrial photodermatoses, such as can arise from handling tar, coal and pitch.

Moreover, there is a connection between the exposure of the skin to UV-A radiation and its aging. In addition, it has been proved that a greater exposure of the skin to UV-A radiation, in particular in the case of sensitivity, of genetic origin, to UV means a greater risk of contracting skin cancer. For all these reasons, it appears necessary to develop agents which also offer effective protection against UV-A radiation.

The aim was, therefore, to provide an agent for protection against light, especially an agent based on an oil-in-water emulsion, which also offers effective protection against UV-A radiation. For this, it is necessary to provide an oil-soluble UV-A filter which fulfils the following conditions:

(1) an absorption maximum at 340 nm;
(2) a high specific extinction $E_1^1$ (this means: economy in use, less active compound in the recipe and a lower toxicological risk, since less substance comes into contact with the skin);
(3) an excellent solubility in oil (no precipitation at relatively low temperatures, for example during transportation or use in the case of winter sports);
(4) stability to UV radiation;
(5) stability to oxidation;
(6) stability to heat;
(7) stability to changes in pH;
(8) toxicological acceptability;
(9) no pronounced intrinsic odour;
(10) no distinct intrinsic colour;
(11) as far as possible, liquid (easy incorporation into the recipe); and
(12) ability to be synthesised in adequate purity using agents which are customary in industry.

UV-A filters for cosmetic purposes are indeed in principle not new. However, the known UV-A filters do not fulfil the above-mentioned conditions to an adequate extent, especially with regard to the absorption maximum, the value of the specific extinction $E_1^1$ and the solubility in oil.

According to the present invention we provide an agent for protection against light comprising an oil or wax having dissolved therein a 4-methoxybenzylidenecyanoacetic acid ester of the general formula

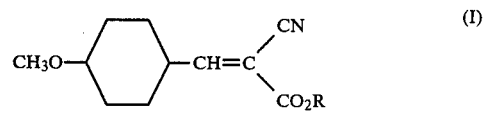

in which

R denotes an n-hexyl, n-octyl or n-decyl radical or a primary isoalkyl radical with 9 or 10 carbon atoms.

Surprisingly the ester of formula (I) may fulfil the abovementioned conditions in an optimum manner.

By primary iso-alkyl radicals R (formula I) there are preferably understood those radicals which are derived from the corresponding iso-alkyl alcohols, which are accessible by hydroformylation of oligo-olefines and subsequent hydrogenation of the hydroformylation product. Isomer mixtures occur in the alcohols thus produced, which, with regard to the corresponding radicals R, gives rise to a corresponding isomer mixture or an isomer mixture, the ratio of which has been shifted in the course of the synthesis.

The compounds of the formula I are synthesised by processes analogous to those known from the literature (Knoevenagel condensation reaction), from 4-methoxybenzaldehyde and cyanoacetic acid esters [for example Organikum, 1967 edition, page 444].

The corresponding cyanoacetic acid esters are obtained by trans-esterifying a readily accessible cyanoacetic acid ester, for example the ethyl or methyl ester, with the appropriate alcohol.

Compounds of the general formula (II)

are already known from German Pat. Specification No. 1,087,902 and U.S. Pat. No. 3,275,520. If the conditions listed above for a UV-A filter are applied to this broad class of compounds (II), it is found, surprisingly, that only those few compounds of the general formula (I) which are according to the invention fulfil these conditions:

1. Ar=an aromatic radical: for reasons of solubility and in order to achieve a high specific extinction $E_1^1$, this radical must be as small as possible. If this requirement is combined with that of a stable molecule the phenyl radical is the optimum radical. Heterocyclic radicals, such as, for example, furane or pyrrole, are not sufficiently stable to oxidation.

2. Substituents on the aromatic radical:
   (a) Position and number: ortho-substitution gives rise to only a relatively low extinction; meta-substitution gives rise to absorption at wavelengths which are too short; and para-substitution gives rise to high extinction and absorption at long wavelengths. For the reasons given above, if several substituents on one nucleus are under discussion, only those in the meta-position and para-position can be considered. However, meta-para-disubstituted compounds exhibit a lower extinction than para-monosubstituted compounds. Para-monosubstitution is thus the optimum substitution.

(b) Nature of the substituents in the para-position: halogen and alkyl give an absorption at wavelengths which are too short; amino groups and alkylamino groups give an absorption at wavelengths which are too long; a hydroxyl group gives rise to inadequate stability; O-acyl groups give an absorption at wavelengths which are too short; and a methoxy group gives rise to optimum properties.

3. The radical R (H. alkyl or aryl): R must be H in order to achieve an optimum specific extinction.

For spectroscopic reasons, after these limitations to a 4-methoxyphenyl radical and R=H, only the combinations cyano group/ester group and cyano group/alkylamide group still remain for the combination X/Y. For reasons of solubility and of the specific extinction $E_1^1$, the cyano group/alkylamide group combination is inferior to the first combination, so that the optimum combination is the cyano group/ester group combination according to the invention.

These effects can be clearly seen from Table 1 which follows.

However, surprisingly, a sensitive dependence of the solubility on the chain length and on the branching of the radical R in the ester group has been found in the case of the compounds according to the invention, so that even variations from branched to unbranched or variations from $C_n$ to $C_{n+1}$ give rise to drastic differences in solubility.

It is thus in no way possible to use any desired alkyl radical, but the few alkyl radicals according to the invention, listed quite specifically for formula I, must be employed.

These dependencies are expressed in Table II, from which further outstanding properties of the compounds according to the invention, such as melting point and extinction, can also be seen.

It was also completely surprising, that the compounds according to the invention are toxicologically acceptable in spite of their lipophilic character, which should result in penetration and resorption through the skin being facilitated.

UV-A filters for cosmetic and dermatological agents for protection against light are not new. Thus, for example, the sodium salt of 2,2'-dihydroxy-4,4'-dimethoxybenzophenone-5-sulphonic acid (1), 2,2',4,4'-tetrahydroxybenzophenone (2) and dianisoylmethane (3) are commercially available.

TABLE 1

|   | Wavelength $\lambda_{max}$ | Molar extinction $\epsilon$ | Specific extinction $E_1^1$ | Stability |
|---|---|---|---|---|
| 2-Methoxybenzylidenecyanoacetic acid methyl ester | 354 (297) | 10,300 (12,100) | 470 (560) | + |
| 3-Methoxybenzylidenecyanoacetic acid methyl ester | 299 | 15,300 | 710 | + |
| 3-Hydroxybenzylidenecyanoacetic acid methyl ester | 303 | 18,200 | 900 | — |
| 3-Hydroxybenzylidenemalonic acid diethyl ester | 282 | 20,300 | 770 | — |
| 4-Methoxybenzylidenecyanoacetic acid methyl ester | 340 | 29,300 | 1,350 | + |
| 4-Methoxybenzylidenemalonic acid diisobutyl ester | 312 | 24,800 | 740 | + |
| 4-Methoxybenzylidenecyanoacetic acid amide | 332 | 24,300 | 1,200 | + |
| 4-Methoxybenzylidenecyanoacetic acid diisobutylamide | 325 | 15,900 | 510 | + |
| 4-Methoxybenzylideneacetoacetic acid ethyl ester | 316 | 19,000 | 770 | — |
| 4-Hydroxybenzylidenecyanoacetic acid methyl ester | 348 | 27,300 | 1,350 | — |
| 4-Hydroxy-3-methoxybenzylidenecyanoacetic acid methyl ester | 366 | 22,400 | 960 | — |
| 4-Hydroxy-3-methoxybenzylidenemalonic acid diethyl ester | 332 | 20,750 | 630 | — |
| 4-Hydroxy-3-methoxybenzylideneacetoacetic acid ethyl ester | 340 | 18,200 | 690 | — |
| 3,4-Dimethoxybenzylidenecyanoacetic acid methyl ester | 360 | 24,000 | 970 | +— |
| 3,4-Dimethoxybenzylidenemalonic acid diethyl ester | 308 | 20,500 | 670 | +— |
| 4-Dimethylaminobenzylidenecyanoacetic acid methyl ester | 421 | 19,900 | 870 | — |
| 4-Dimethylaminobenzylidenemalonic acid dimethyl ester | 375 | 31,400 | 1,200 | — |
| 4-Dimethylaminobenzylidenemalonic acid diamide | 369 | 20,400 | 870 | — |
| 4-Methacryloxybenzylidenecyanoacetic acid methyl ester | 312 | 23,000 | 1,230 | — |
| 4-Chlorobenzylidenecyanoacetic acid methyl ester | 313 | 20,900 | 940 | + |
| 3-Aminobenzylidenecyanic acid methyl ester | 310 | 16,800 | 830 | — |
| 4-Methylbenzylidenecyanoacetic acid methyl ester | 317 | 25,000 | 1,230 | + |
| Furfurylidenecyanoacetic acid methyl ester | 337 | 27,000 | 1,530 | — |
| α-Cyano-β-methyl-β-(4-methoxyphenyl)-acrylic acid methyl ester | 318 | 10,900 | 460 | + |
| α-Cyano-β,β-diphenyl-acrylic acid methyl ester | 298 | 14,000 | 520 | + |

After it had thus been found that 4-methoxybenzylidenecyanoacetic acid esters are the optimum compounds with respect to the spectral data and the stability, it could be assumed that it would now be relatively simple to achieve suitable solubility in oil, since the solubility in oil of relatively large organic molecules usually increases as the chain length of the aliphatic radical linked thereto increases.

The properties of these known compounds are compared with those of the derivatives of the formula I according to the invention in Table II. The superior properties of the compounds according to the invention for the intended use aimed for can be seen from this comparison. The known compounds (1-3) are unsuitable from the point of view of solubility. (1) and (2) have a significantly lower specific extinction. In contrast, (3) indeed has a high specific extinction, but this is at too long a wavelength, so that the important region between 320 and 340 nm is not completely screened off.

TABLE II

| Compound of the formula I according to the invention; R | Wavelength $\lambda_{max}$ (nm) | Molar extinction $\epsilon$ $\frac{1000 \text{ cm}^2}{M}$ | Specific extinction $E_1^1$ | Solubilities at room temperature | | Melting point (°C.) |
|---|---|---|---|---|---|---|
| | | | | (20-25° C.) in Groundnut oil (%) | Groundnut oil/ liquid paraffin 1:9 (%) | |
| n-Butyl | 342 | 28,300 | 1,090 | 17 | 3 | 41-43 |
| n-Pentyl | 341 | 28,600 | 1,050 | 6-7 | 1.4 | 59-61 |
| n-Hexyl* | 342 | 28,500 | 990 | 00 | 90 | oil |
| n-Heptyl | 341 | 28,300 | 940 | 33 | 7 | 34-36 |
| n-Octyl* | 341 | 30,500 | 970 | 00 | 90 | 30 |
| n-Nonyl | 341 | 30,000 | 910 | 55 | 10 | 32 |
| n-Decyl* | 341 | 27,700 | 810 | 00 | 00 | oil |
| n-Dodecyl | 342 | 28,450 | 770 | 14 | −3 | 45-47 |
| iso-Hexyl | 342 | 26,000 | 910 | 10 | −2 | 60-63 |
| iso-Octyl | 341 | 28,500 | 910 | 45 | −7 | 30-31 |
| iso-Nonyl* | 341 | 28,400 | 860 | 00 | 80 | oil |
| iso-Decyl* | 341 | 27,000 | 790 | 00 | 00 | oil |
| Known compounds | | | | | | |
| (1) | 330 | 5,920 | 160 | — | — | >350 |
| (2) | 351 | 15,900 | 645 | 0.8 | — | 195 |
| (3) | 362 | 36,000 | 1,270 | 1 | — | 116.7 |

00 = miscible in all proportions
— = virtually insoluble
* = compound according to the invention UV kinetic studies gave an excellent stability of the compounds according to the invention to UV radiation. The following details may serve to illustrate the tolerance: the 14 day LD 50 is 20.76 ml/kg for the iso-nonyl ester of the compound I and 5.71 ml/kg for the n-hexyl ester. No skin irritation could be detected in rabbits.

The invention thus relates to an agent for protection against light which contains, in an oil phase, at least one of the compounds of the formula I as a UV-A filter for protecting the skin against UV-A radiation, in addition to other suitable cosmetic or dermatological additives. The agent for protection against light can be used, for example, as protection against natural solar radiation, for example during leisure or during a period spent in sunlight for industrial reasons, against sources of artificial light, for example a sun-ray lamp and a solarium, and for the treatment of pathogenic sensitivity, for example genetic or industrial, towards UV-A radiation.

The following compounds are specific oil-soluble UV-A filters which are outstandingly suitable for the intended use described: 4-methoxy-benzylidene-cyanoacetic acid n-hexyl ester, 4-methoxy-benzylidene-cyanoacetic acid n-octyl ester, 4-methoxy-benzylidene-cyanoacetic acid n-decyl ester, 4-methoxy-benzylidene-cyanoacetic acid isononyl ester and 4-methoxy-benzylidene-cyanoacetic acid isodecyl ester.

The n-hexyl ester and the iso-nonyl ester are particularly outstandingly suitable.

The agents according to the invention can be in the form of a liquid which consists of a single phase and which contains a single solvent or a mixture of solvents, for example an oil/alcohol mixture. They can also be in the form of a dispersion, an oil-in-water emulsion or water-in-oil emulsion, a homogeneous paste, a semi-solid product or a product which contains a propellant. They can constitute agents for protection against sunlight, such as oil, lotions and aerosols (of the oil, foam or "spray" type), and also a cream for normal or dry skin, a milk, lipsticks or any other customary cosmetic or dermatological formulation.

Constituents which may be mentioned for the agents, according to the invention, defined above in more detail are, in particular: lanolin, vaseline, triglycerides of fatty acids, polyethylene glycols, ethoxylated fatty alcohols, esters, such as isopropyl palmitate, isopropyl myristate, isopropyl stearate, oleyl oleate and butyl stearate, animal, vegetable, synthetic or mineral oils, fatty alcohols, lower alcohols and organic and mineral waxes. These constituents are used in amounts of about 1-97% by weight.

The compounds of the formula I according to the invention are used in the agents, according to the invention, for protection against light in a concentration of 0.2 to 10% by weight, relative to the weight of the formulation, and preferably in a concentration of 0.5 to 6%, the remainder of the formulation being made up to 100% by weight by, on the one hand, the customary cosmetic or dermatological ingredients and, on the other hand, the solvent or a mixture of the solvents which are contained in the entire formulation.

Cosmetic and dermatological additives which may be mentioned are thickeners, irritation-relieving and anti-inflammatory agents, superfatting agents, softeners, wetting agents, surface-active agents and preservatives, antifoaming agents, perfumes and aroma substances or any other usable additive such as is customary, in cosmetics or dermatology, for the intended use aimed for.

The agents according to the invention can be colourless, or coloured with those colorants and/or pigments which are usually used for agents for protection against sunlight, and in particular with iron oxides, in proportions of about 0.001 to 0.050% by weight, relative to the total weight of the formulation.

If the agent according to the invention contains a propellant, the propellants used are, in particular, those based on chloro-fluoromethanes.

In addition to the UV-A filters of the formula I, the formulations according to the invention can also contain 0.2 to 10% by weight UV-B filters, such as; p-aminobenzoic acid, p-aminobenzoic acid ethyl ester oxyethylated with 25 mols of ethylene oxide, p-aminobenzoic acid ethyl ester N-propoxylated with 2 mols of propylene oxide, p-dimethylaminobenzoic acid ethyl ester, p-dimethylaminobenzoic acid amyl ester, p-dimethylaminobenzoic acid 2-ethylhexyl ester, p-dimethylaminobenzoic acid isoamyl ester, p-dimethylaminobenzoic acid hexyl ester, p-dimethylaminobenzoic acid heptyl ester, salicylic acid methyl ester, dipropylene glycol salicylate, salicylic acid homomenthyl ester, salicylic acid 2-ethylhexyl ester, triethanolamine salicylate, N-acetylanthranilic acid trimethylcyclohexyl ester, anthranilic acid menthyl ester, cinnamic acid benzyl ester, cinnamic acid menthyl ester and homomenthyl ester, cinnamic acid octyl ester, p-isopropylcinnamic acid ethyl ester, diisopropylcinnamic acid ethyl ester, diisopropylcinnamic acid methyl ester, p-methoxycinnamic acid isoamyl ester, p-methoxycinnamic acid isopropyl ester, p-methoxycinnamic acid propyl ester, p-methoxycinnamic acid 2-ethylhexyl ester, p-methoxycinnamic acid cyclohexyl ester, p-methoxycinnamic acid and salts, α-cyano-β-phenylcinnamic acid ethyl ester, α-cyano-β-phenylcinnamic acid 2-ethylhexyl ester, 2-hydroxy-4-methoxy-benzophenone, 4-phenylbenzophenone, 4-phenyl-benzophenone-2-carboxylic acid 2-ethylhexyl ester, 2,2'-dihydroxy-4-methoxy-benzophenone, 2-hydroxy-4-n-octyloxybenzophenone, 2,2'-dihydroxy-4,4'-dimethoxy-benzophenone, 2-hydroxy-4-methoxy-benzophenone-5-sulphonic acid, sodium 2,2'-dihydroxy-4,4'-dimethoxy-benzophenone-5-sulphonate, 2,4-dihydroxy-benzophenone, 2,2'-4,4'-tetrahydroxy-benzophenone, 2-hydroxy-4-methoxy-4'-methylbenzophenone, 3-(4-methylbenzylidene)-D,L-camphor, sodium 3-(4-methylbenzylidene)-D,L-camphor-sulphonate, 3-benzylidene-D,L-camphor, m-digallic acid trioleate, 2-phenylbenzimidazole-5-sulphonic acid, sodium 3,4-dimethoxyphenolglyoxylate, β-imidazole-4(5)-acrylic acid (urocanic acid), 2-phenyl-5-methyl-benzoxazole, dibenzalazine, dianisoylmethyne, 5-(3,3-dimethyl-2-norbornylidene)-3-pent-2-en-2-one, (2'-hydroxy-5'-methylphenyl)-benzotriazole and 1-phenyl-3-(3-pyridyl)-1,3-propanedione.

2-Phenyl-5-methyl-benzoxazole, 2-phenyl-benzimidazole-5-sulphonic acid and 4-methoxy-cinnamic acid iso-amyl ester are particularly suitable UV-B filters.

The following Examples illustrate agents of the present invention in the form of cosmetic or dermatogical preparations.

EXAMPLE 1

| Oil for protection against sunlight | |
| --- | --- |
| p-Methoxy-benzylidene-cyanoacetic acid n-hexyl ester | 3% |
| Liquid paraffin | 37% |
| Isopropyl palmitate | 60% |
| Perfume oil | q.s. |

EXAMPLE 2

| Oil for protection against sunlight | |
| --- | --- |
| p-Methoxy-benzylidene-cyanoacetic acid n-octyl ester | 2% |
| p-Methoxy-cinnamic acid isoamyl ester | 2% |
| Groundnut oil | 46% |
| Liquid paraffin | 50% |
| Perfume oil | q.s. |

The oils for protection against sunlight are prepared by mixing the components indicated.

EXAMPLE 3

Lipsticks

| Commercially available lipstick composition | 94% |
| --- | --- |
| p-Methoxy-benzylidene-cyanoacetic acid n-hexyl ester | 3% |
| p-Methoxycinnamic acid isoamyl ester | 3% |

The lipstick composition is melted and mixed with the other two components. The composition is cast in cooled lipstick moulds and, after cooling, the moulded articles are removed.

EXAMPLE 4

| Spray for protection against sunlight | |
| --- | --- |
| Mixture according to Example 1 | 40% |
| Propellant gas mixture of trichlorofluoromethane and dichlorofluoromethane 70:30 | 60% |

The two components are filled into an appropriate aerosol container.

EXAMPLE 5

| | Cream for protection against sunlight, of the oil-in-water type | |
| --- | --- | --- |
| A. | Fatty alcohol polyglycol ether based on stearyl alcohol and cetyl alcohol | 7.5% |
| | Duck uropygial gland fat (synthetic) | 5.0% |
| | Isopropyl palmitate | 6.0% |
| | Caprylic/capric triglyceride | 11.0% |
| | Cetyl stearyl alcohol | 2.0% |
| | Silicone oil cP 100 | 0.5% |
| | p-Methoxy-benzylidene-cyanoacetic acid iso-nonyl ester | 2.0% |
| B. | Demineralised water | 66.0% |
| | Perfume oil | q.s. |
| | Preservative | q.s. |

The components are melted and mixed, at 70° C. The mixture is added in portions, whilst stirring, to the water, which is warmed to about 75° C. The emulsion formed is cooled slowly, and with further stirring, to room temperature.

EXAMPLE 6

| | Milk for protection against sunlight | |
| --- | --- | --- |
| A. | Colloidally dispersed mixture of cetyl stearyl alcohol and sodium cetyl-stearyl-sulphate with a non-ionic emulsifier | 3.15% |
| | Decyl oleate | 15.00% |
| | 4-Methoxy-benzylidene-cyanoacetic acid n-decyl ester | 2.00% |
| | (the oil can also contain the iso-decyl ester instead of the n-decyl ester) | |
| B. | Water | 79.85% |
| | Perfume | q.s. |
| | Preservative | q.s. |
| | The preparation is as for Example 5. | |

What is claimed is:

1. A composition for protection against UV light in the UVA region having a wavelength range from 320 to 400 nm, comprising an oil or wax carrier having dissolved therein an effective UVA absorbing amount of a 4-methoxybenzylidenecyanoacetic acid ester of the formula

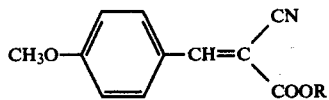

in which

R denotes a n-hexyl, n-octyl or n-decyl radical or a primary isoalkyl radical with 9 or 10 carbon atoms.

2. A composition according to claim 1, in which the ester has a concentration of 0.2 to 10% by weight.

3. A composition according to claim 1 or 2, in which the ester has a concentration of 0.5 to 6% by weight.

4. A composition according to claim 1, in which the ester of formula (I) is 4-methoxybenzylidenecyanoacetic acid n-hexyl ester.

5. A composition according to claim 1, in which the ester of formula (I) is 4-methoxybenzylidenecyanoacetic acid isononyl ester.

6. A composition according to claims 1, 4 or 5 containing 0.2 to 10% by weight UV-B filters.

7. A composition according to claim 6, in which the UV-B filter is 2-phenyl-5-methyl-benzoxazole, 2-phenyl-benzimidazole-5-sulphonic acid or 4-methoxy-cinnamic acid isoamyl ester.

8. A composition according to claim 1 containing one or more cosmetic or dermatological additives.

* * * * *